United States Patent [19]
Chen et al.

[11] Patent Number: 6,096,066
[45] Date of Patent: Aug. 1, 2000

[54] CONFORMAL PATCH FOR ADMINISTERING LIGHT THERAPY TO SUBCUTANEOUS TUMORS

[75] Inventors: James C. Chen, Bellevue, Wash.; Brent Wiscombe, Mesa, Ariz.

[73] Assignee: Light Sciences Limited Partnership, Issaquah, Wash.

[21] Appl. No.: 09/151,844

[22] Filed: Sep. 11, 1998

[51] Int. Cl.[7] .................................................. A61N 5/00
[52] U.S. Cl. .............................................. 607/88; 607/91
[58] Field of Search .................................. 604/20, 19, 21, 604/304, 290; 606/10, 20, 6–9, 27; 607/81–92

[56] References Cited

U.S. PATENT DOCUMENTS

| | | | |
|---|---|---|---|
| 4,787,888 | 11/1988 | Fox | 604/20 |
| 4,919,648 | 4/1990 | Sibalis | 604/20 |
| 4,921,475 | 5/1990 | Sibalis | 604/20 |
| 4,957,481 | 9/1990 | Gatenby | 604/20 |
| 4,976,705 | 12/1990 | Aki et al. | 604/304 |
| 5,259,380 | 11/1993 | Mendes et al. | 607/115 |
| 5,261,874 | 11/1993 | Castle | 604/4 |
| 5,298,018 | 3/1994 | Narciso, Jr. | 604/21 |
| 5,358,503 | 10/1994 | Bertwell et al. | 606/27 |
| 5,474,528 | 12/1995 | Meserol | 604/20 |
| 5,484,803 | 1/1996 | Richter | 514/410 |
| 5,489,279 | 2/1996 | Meserol | 604/290 |
| 5,505,726 | 4/1996 | Meserol | 606/9 |
| 5,616,140 | 4/1997 | Prescott | 606/10 |
| 5,705,518 | 1/1998 | Richter et al. | 514/410 |
| 5,709,653 | 1/1998 | Leon | 604/20 |
| 5,736,563 | 4/1998 | Richter | 514/410 |
| 5,860,967 | 1/1999 | Zavislan | 606/9 |
| 5,913,883 | 6/1999 | Alexander et al. | 607/88 |

FOREIGN PATENT DOCUMENTS

| | | | |
|---|---|---|---|
| WO93/21842 | 11/1993 | WIPO | A61B 17/36 |
| WO94/15666 | 12/1994 | WIPO | A61N 1/00 |

OTHER PUBLICATIONS

Bolin, Frank P., Luther E. Preuss, Roy C. Taylor, and Robert J. Ference. "Refractive index of some mammalian tissues using a fiber optic cladding method." *Applied Optics*. vol. 28, No. 12, Jun. 15, 1989. pp. 2297–2304.

Dougherty, Thomas J., Jerome E. Kaufman, Abraham Goldfarb, Kenneth R. Weishaupt, Donn Boyle, and Arnold Mittleman. "Photoradiation Therapy for the Treatment of Malignant Tumors." Reprinted from *Cancer Research*. vol. 38, Aug. 1978. pp. 2628–2635.

Dougherty, Thomas J., Gilbert Lawrence, Jerome H. Kaufman, Donn Boyle, Kenneth R. Weishaupt, and Abraham Goldfarb. "Photoradiation in the Treatment of Recurrent Breast Carcinoma." Reprinted from *Journal of the National Cancer Institute*. vol. 62(2), Feb. 1979. pp. 231–237.

Robinson, Kevin. "Coating Method Makes Molecule–Thick Layers." *Photonics Spectra*, Technology World. Jun. 1998. p. 54.

*Primary Examiner*—Linda C. M. Dvorak
*Assistant Examiner*—Ahmed Farah
*Attorney, Agent, or Firm*—Ronald M. Anderson

[57] ABSTRACT

A flexible patch provided with a plurality of light sources mounted in spaced-apart array on its undersurface and covered with an optically transparent polymer material. The light sources are energized with an electrical current supplied by a flexible polymer battery, which is preferably rechargeable. Electrical current is conveyed through a lead that extends from the flexible battery to the flexible patch and then through an electrical circuit that includes a plurality of conductive traces formed using a conductive ink applied to the surface of a flexible substrate that supports the light sources. The thickness of the flexible patch at its maximum is less than 1.0 millimeters. The light sources can be separately grouped, and the electrical current supplied to each group individually controlled to achieve a desired light intensity and/or duration exposure to the light therapy over different portions of the undersurface of the flexible patch and different portions of the treatment site. An adhesive applied to the treatment site on the patient's body or on the undersurface of the flexible patch is used to mount the flexible patch to the treatment site. A plurality of slots that extend through the flexible substrate provide passages for air and moisture and enable the flexible substrate to freely and more readily conform to irregular, non-planar shapes of the treatment site. The flexible substrate can also be adhesively secured to a non-planar surface within a patient's body to render the light therapy internally.

28 Claims, 5 Drawing Sheets

CONFORMAL PATCH FOR ADMINISTERING LIGHT THERAPY TO SUBCUTANEOUS TUMORS

FIELD OF THE INVENTION

This invention generally relates to apparatus and a method for delivering light therapy to a patient from an external array of light sources, and more specifically, to a flexible panel of light emitting sources that is adapted to conform around irregular portions of a patient's body to deliver light therapy to an internal site.

BACKGROUND OF THE INVENTION

Photodynamic therapy (PDT) is now recognized as an effective method for destroying abnormal tissue or tumors. To implement PDT, a photoreactive agent such as a hematoporphyrin is applied and is preferentially absorbed by the abnormal tissue, but to a much lesser extent by normal tissue. The photoreactive agent has a characteristic light absorption waveband. Light within this absorption waveband is administered to a treatment site where the abnormal tissue is disposed. The light activates the photoreactive agent, which destroys the abnormal tissue, but has much less effect on the surrounding normal tissue. However, it is common for the photoreactive agent to sensitize normal tissue, such as skin, for a period of time ranging, for example, from 48 hours to six weeks (depending upon the specific photoreactive agent administered), during which the patient should avoid exposure to sunlight or other bright light, since such exposure can damage the normal tissue.

It is also possible to treat subcutaneous primary and metastatic tumors with PDT using an external light source that emits light within a waveband that readily penetrates the cutaneous layer overlying the tumors. A principle drawback of using external light sources to administer the light therapy for either of these types of tumors is the effect that the therapy has on the surrounding normal skin, which is often photosensitive during the administration of the light therapy. Administering PDT with an external light source while the surrounding normal skin is affected by the photoreactive agent risks damage to the cutaneous layer, with possible risk of infection and increased risk of causing pain at the treatment site. While damage to the normal cutaneous tissue overlying a tumor is possible, it is preferable to minimize the area where such damage can occur.

A problem with administering light to an internal treatment site using a conventional external light source can arise if the internal tumor mass is asymmetrical. If light is administered from an external source through the overlying cutaneous layer, some portions of the tumor will likely receive too much light, and some portions will receive too little light to achieve an optimal result. It would be desirable to administer light to a cutaneous or subcutaneous treatment site for an extended period of time, and to limit the area over which the light is administered to the region of the treatment site. Thus, the patient should preferably be ambulatory during the treatment and not constrained to sit in a doctor's office while receiving the PDT. To facilitate therapy to any part of the body using an external light source, it is preferable for the light source to be fully portable and carried attached to the patient's body. Since many areas of the human body are non-planar and because a subdermal tumor can cause a substantial swelling of the cutaneous layers overlying the tumor, producing a convex lump on the skin, the light source should be able to conform to the shape of the treatment site by wrapping around such a non-planar surface and being adhesively secured in place.

Achieving a specific light dosimetry, i.e., the delivery of a desired intensity of light for a desired interval during PDT is another problem that is not properly addressed by prior art external light sources. An ambulatory external source of light suitable for administering prolonged, accurate illumination of irregular surfaces and capable of providing different light intensity to different regions of the treatment site is not known in the prior art. It will be evident that there is a clear need for such a device and a corresponding method for administering light therapy in this manner.

SUMMARY OF THE INVENTION

In accordance with the present invention, a light therapy patch adapted to conform to a non-planar portion of a patient's body at a treatment site to which the therapy is to be administered. The light therapy patch includes a flexible substrate formed of a dielectric material. Included within the flexible substrate are a plurality of open perforations that extend therethrough to provide ventilation paths enabling movement of air and moisture. A power source is coupled to the patch for supplying an electrical current at a desired voltage to a plurality of flexible conductive traces that are applied to at least one surface of the flexible substrate. The flexible conductive traces define an electrical circuit for conveying an electrical current provided by the power source to defined portions of the flexible substrate. A plurality of light emitting sources are mounted to the flexible substrate in a spaced-apart array and are electrically coupled to the conductive traces to receive the electrical current. The electrical current energizes the plurality of light emitting sources so that they emit light to provide the light therapy at the treatment site.

The plurality of conductive traces are preferably produced by applying a conductive material, media, or fluid (e.g., a conductive ink) to the surface of the flexible substrate. If a conductive fluid is used, the conductive traces are formed when the conductive fluid sets, becoming a flexible solid.

An adhesive is provided to secure the flexible substrate to the non-planar portion of the patient's body, so that the flexible substrate conforms to the non-planar portion. The adhesive is applied either to the non-planar portion of the patient's body before applying and conforming the flexible substrate to said non-planar portion, or is disposed on a surface of the flexible substrate that faces toward the non-planar portion of the patient's body when the flexible substrate is applied thereto.

Optionally, a light reflective layer disposed over an outwardly facing surface of the flexible substrate is provided to reflect light emitted by the light sources back toward the treatment site. Also, an optically transparent coating is preferably applied over the plurality of light sources mounted on the flexible substrate to provide protection.

The power source preferably comprises a flexible polymeric battery. A lead connects the flexible polymeric battery to the plurality of conductive traces, and the flexible polymeric battery is carried by the patient separate from the flexible substrate during administration of the light therapy.

In one form of the invention, the plurality of light emitting sources emit a broad spectrum light. The plurality of light emitting sources are preferably incandescent, halogen, fluorescent, electroluminescent sources, or some type of light emitting diodes, such as polymeric light emitting diodes, organic light emitting diodes, or metallic light emitting diodes.

The electrical circuit on the patch preferably comprises a plurality of parallel circuits conveying the electrical current to groups of the light sources, so that each group is separately energized by the electrical current. A microcontroller is coupled to the electrical circuit for separately controlling the electrical current supplied to each group of light sources to control an intensity of the light administered to different regions of the treatment site.

Another aspect of the present invention is directed to a method for administering a light therapy to a treatment site. The steps of this method are generally consistent with the functions of the elements of the light therapy patch discussed above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

DESCRIPTION OF THE PREFERRED EMBODIMENT

Figure 1:
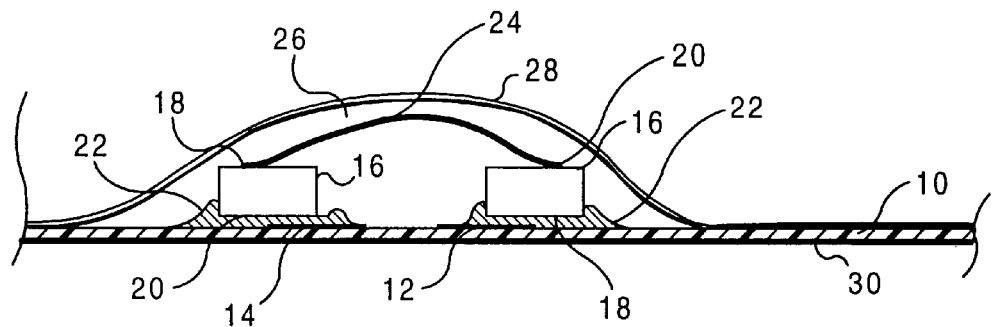
FIG. 1 is a cross-sectional side elevational view of a portion of a flexible patch for administering light therapy, in accordance with the present invention.

In FIG. 1, a small portion of a flexible substrate 10 is illustrated that is used in creating a conformal flexible patch adapted to provide a close fit over a non-planar portion of a patient's body for treating external or subcutaneous abnormal tissue at that treatment site by administering light therapy. Further details that disclose how flexible substrate 10 is able to more readily conform to irregularly shaped portions of the patient's body to provide a close fit are disclosed below. Flexible substrate 10 is less than 0.1 millimeter thick in a preferred form of the invention and is fabricated from a highly flexible thin film polymer such as silicone or polyurethane.

Figure 2:
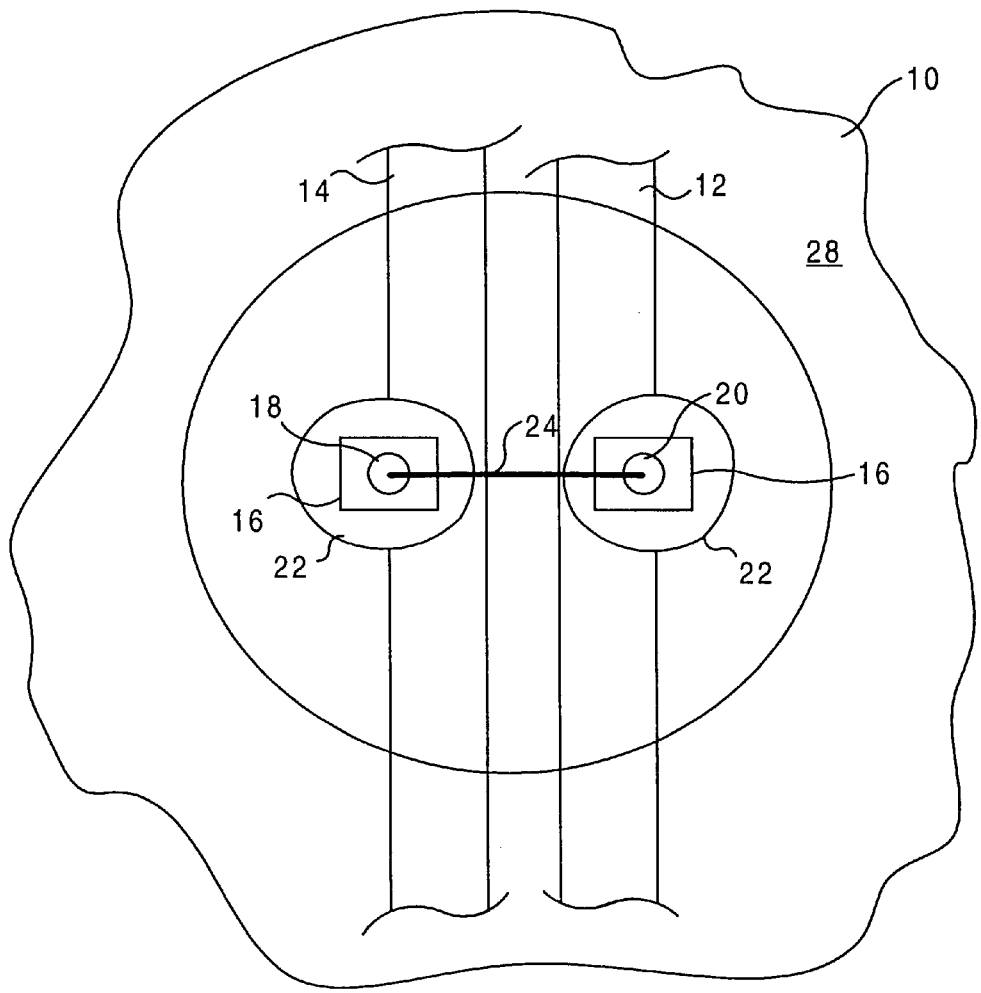
FIG. 2 is a schematic plan view of an undersurface of a portion of the flexible patch.

Conductive traces 12 and 14 are formed on a surface of flexible substrate 10 that is adapted to face toward a treatment site on the patient's body to which light therapy is to be administered. These conductive traces are preferably formed using a conductive ink applied in a liquid form and allowed to set, or some other extremely flexible conductive media. Conductive ink works well for this purpose, since it produces a very thin conductive trace after it dries and is readily applied in any desired configuration to form an electrical circuit on the surface of the flexible substrate. FIG. 2 illustrates portions of electrical traces 12 and 14, where they extend generally parallel to each other; the traces are spaced apart sufficiently to enable two light emitting sources 16 to be mounted on the flexible substrate between the electrical traces and each in electrical contact with one of the electrical traces. Light emitting sources 16 each preferably comprise a broad spectrlum light source such as an incandescent, halogen, fluorescent, or electroluminescent light source, or may comprise either a light emitting diode (LED) or a specialized type of LED, such as a polymeric, an organic, or a metallic LED.

As illustrated in FIGS. 1 and 2, light emitting sources 16 are electrically mounted on conductive trace 12 and conductive trace 14 using a conductive bonding adhesive 22, which is applied to the conductive trace to secure one side of light emitting source 16 to that conductive trace. In the embodiment disclosed in FIGS. 1 and 2, light emitting sources 16 are mounted as pairs disposed adjacent each other, with one light emitting source of the pair being adhesively attached to conductive trace 12, and the other adhesively attached to conductive trace 14 using conductive adhesive 22. An anode 18 of one of the light emitting sources is electrically coupled to conductive trace 12, while a cathode 20 of the adjacent light emitting source of the pair is electrically coupled to conductive trace 14. It will be understood that the relationship between the anode and cathode and the electrical trace to which it is coupled can be switched, so long as the appropriate polarity electrical current is applied to energize the light emitting sources so that they emit light. If the conductive traces are energized with an alternating current (AC), the anodes and cathodes of successive pairs of LEDs will preferably alternate in polarity in regard to their connection to conductive traces 12 and 14. The LEDs connected in one polarity are thus energized during the positive portion of the AC waveform, and those connected in the opposite polarity are energized during the negative portion of the AC waveform.

The two light emitting sources are connected in series using a flywire 24 that extends between the anode of one of the pair of light emitting sources and the cathode of the other. Alternatively, it would be possible to directly connect flywire 24 between one of the light emitting sources and the other conductive trace that it is not adhesively bonded to, so that the two light emitting sources are connected in parallel rather than in series. Other techniques for mounting the light emitting sources to the conductive traces can be used to eliminate the need for flywire 24, for example, by directly connecting terminals (not shown) disposed at each side of the light emitting sources to the respective conductive traces.

Figure 3:
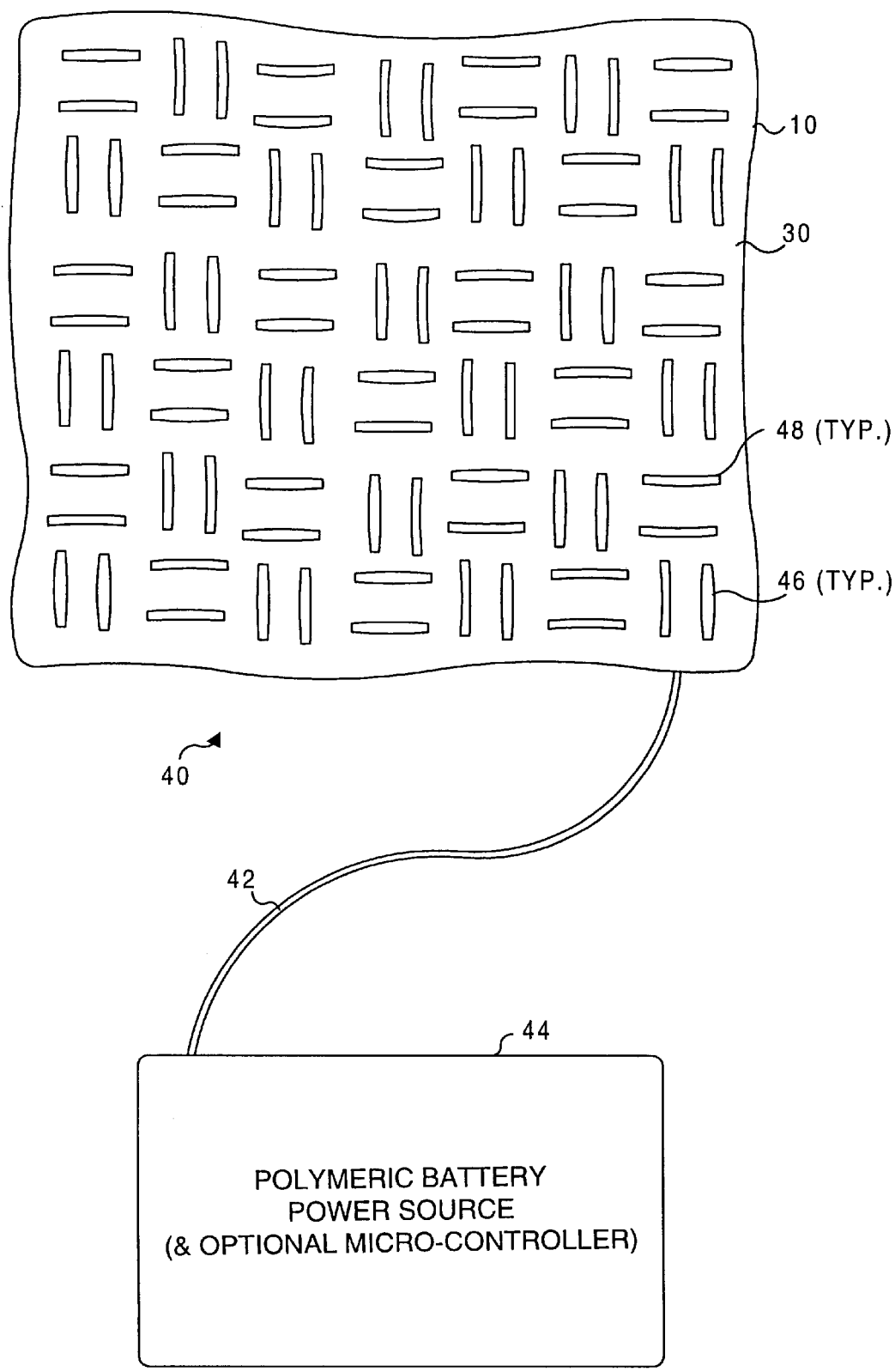
FIG. 3 is a schematic plan view of the outer surface of the flexible patch and a flexible power source used to provide electrical current to the flexible patch.

A droplet 26 of a flexible epoxy or other polymer is applied over each pair of light emitting sources 16 to protect them and flywire 24. This droplet is optically transparent or translucent. Further, the surface of the flexible patch facing inwardly toward the treatment site is preferably coated with a relatively thin layer 28 of silicone to insulate the entire assembly and provide protection to conductive traces 12 and 14 in those areas between droplets 26. It is desirable that this thin layer and the droplet applied over each LED have an index of refraction that is generally matched to that of the patient's skin at the treatment site to which light therapy is to be administered by light emitting sources 16. Preferably the maximum thickness of the flexible patch is less than 1.0 millimeters, which insures the substantial flexibility of the patch. Referring to FIG. 3, a flexible patch 40 fabricated using flexible substrate 10 is illustrated. The light sources mounted on the inwardly facing surface of flexible patch 40 are disposed on the undersurface of the flexible substrate and thus do not show in this Figure.

To enable flexible patch 40 to fully conform to non-planar irregular surfaces on a patient's body, the flexible patch includes a plurality of horizontal slots 48 and vertical slots 46 that extend through the flexible substrate and thin layer 28. Each of these slots comprise open passages through which air and moisture are readily conveyed when flexible patch 40 is applied to the treatment site on the patient's body. By providing such passages, irritation and heat buildup at the treatment site covered by flexible patch 40 are minimized. Perspiration readily passes through these passages comprising horizontal slots 48 and vertical slots 46 so that the patient is more comfortable during an extended period of light therapy provided by the flexible patch and to ensure that the patch remains adherently attached to the treatment site.

As shown in FIG. 3, a polymeric battery power source 44 is coupled to the flexible patch through leads 42. This power source provides the electrical current that energizes each of the light emitting sources mounted on the undersurface of flexible patch 40. Optionally, polymeric battery power source 44 includes a microcontroller. The purpose of the microcontroller is discussed below. A polymeric battery is used in the preferred form of this invention, since it can be more readily conform to the patient's body and be more comfortably carried than a rigid battery source, being flexible and adhesively attached to the patient's body. However, it is also contemplated that more conventional types of batteries may instead be used for providing electrical current to energize the light emitting sources used on flexible patch 40. Clearly, many types of battery packs could be employed to provide the electrical current needed to energize the light emitting sources. It is also contemplated that the polymeric battery (or other type of battery power source that is used) be rechargeable to facilitate use of the flexible patch for an extended period of time by enabling the patient to repetitively recharge the power source as it becomes exhausted.

Assuming that the flexible substrate is optically transparent or at least partially translucent, the outer surface of flexible patch 40 may optionally be coated with a reflective layer 30. This reflective layer will reflect at least some of the light emitted by the light emitting sources back toward the treatment site, thereby increasing the efficiency with which light therapy is administered by the flexible patch.

Figure 4:
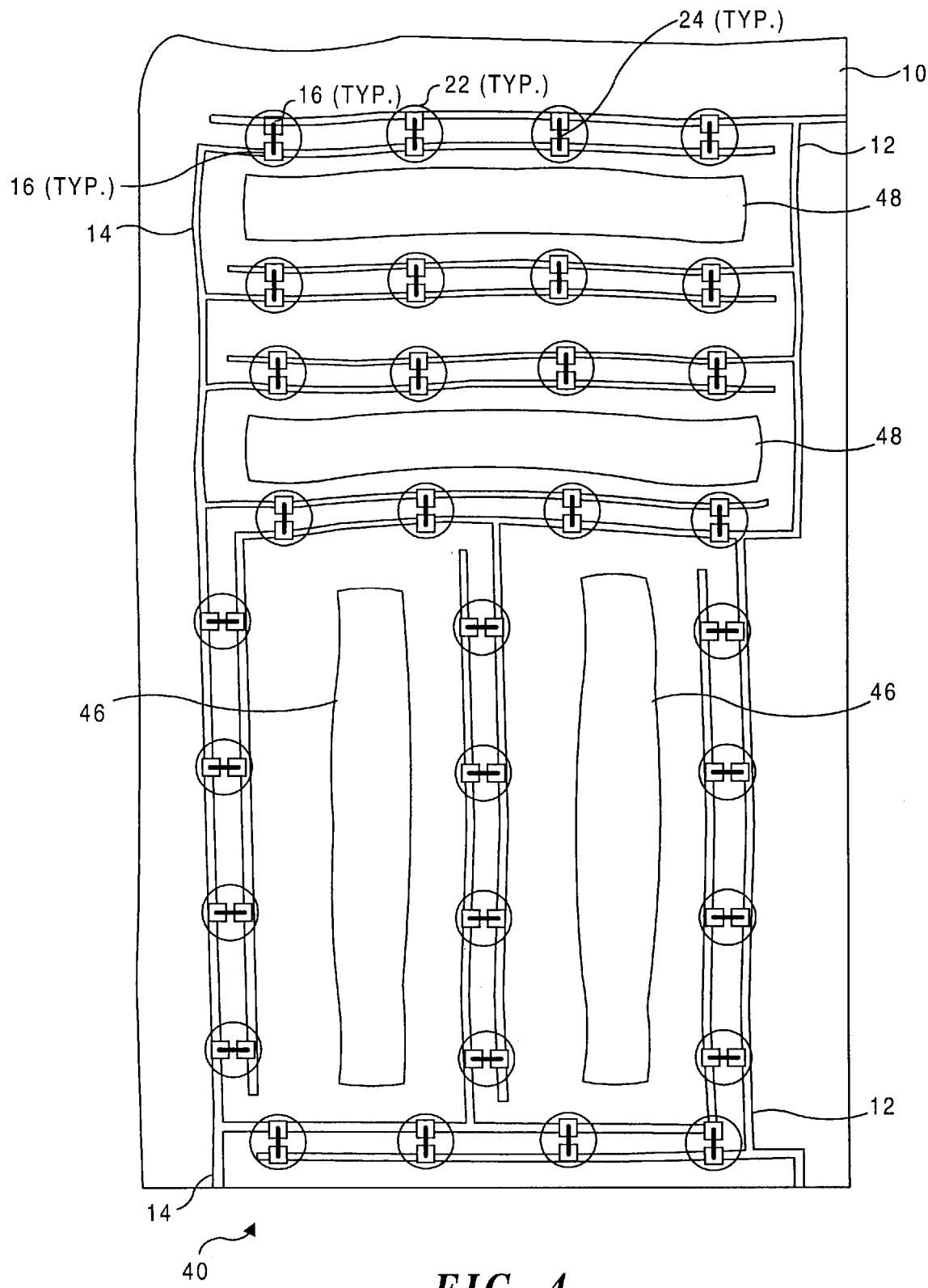
FIG. 4 is an enlarged view of the inner surface on a portion of the flexible patch.

With reference to FIG. 4, a portion of flexible patch 40 is enlarged, showing its undersurface and part of the electrical circuit comprising flexible traces 12 and 14. It will be noted in this Figure that conductive traces 12 and 14 are interspersed with horizontal slots 48 and vertical slots 46 on the undersurface of the flexible patch; the light sources thus comprise an array that is spaced apart over the remaining portion of the undersurface. While a simple pattern of the light sources, horizontal slots 48, and vertical slots 46 is illustrated in FIG. 4, it will be apparent that many other configurations and patterns for electrical circuits comprising flexible traces 12 and 14 on which the light emitting sources are mounted interspersed with horizontal slots 48 and vertical slots 46 can alternatively be provided on the undersurface of the flexible substrate.

Figure 5:
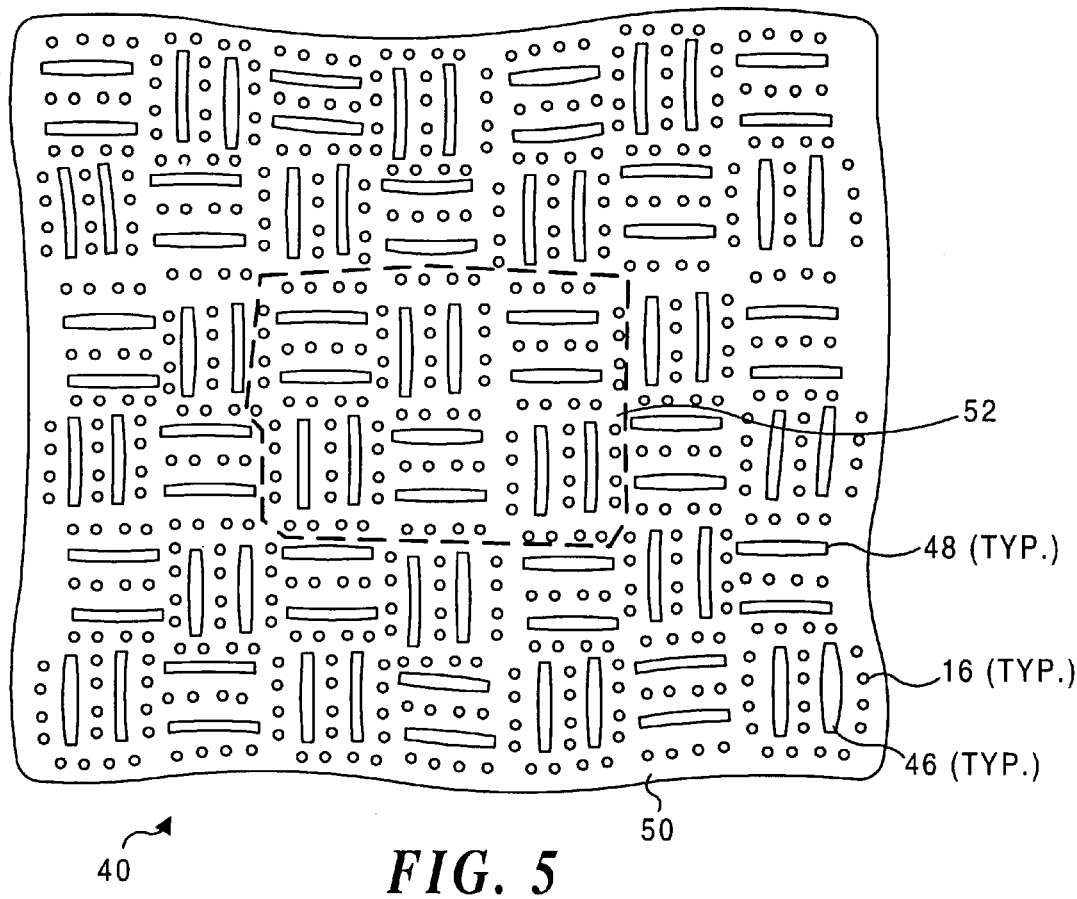
FIG. 5 is a plan view of the inner surface of a flexible patch showing a central group of light sources and a peripheral group of light sources.

It should be noted that a plurality of separately controlled electrical circuits can be provided using conductive traces 12 and 14 so that distinct and separate groups of light emitting sources are defined on the undersurface of flexible patch 40. FIG. 5 illustrates a simple example in which a central group 52 of light emitting sources 16 is defined (encompassed by the dash line). Surrounding central group 52 is a peripheral group 50 of the light emitting sources that are separately controlled. An advantage of this simple configuration is that it provides an option to independently control the electrical current supplied to each different group to control the light intensity produced by the light emitting sources in each group. Thus, for example, central group 52 can be energized longer or with a greater current, compared to that supplied to peripheral group 50, to increase the intensity and/or the duration of the light produced by the central group of light sources. By increasing the light output of central group 52, a more effective treatment of a tumor can be achieved, since the tumor is relatively thicker in its central part, where higher intensity and/or longer duration light therapy should be administered, and thinner around its periphery, where relatively lower intensity and/or shorter duration light therapy should be administered. It will be apparent that additional groups of light sources can be configured and separately controlled to provide substantially more complex patterns to achieve other desired light distribution and control regions over the undersurface of flexible patch 40 as necessary to meet the desired requirements for varying the light intensity over these portions of the treatment site. Also, the shape of any portion of a given group of light emitting sources on the undersurface of the flexible patch can be made substantially different than illustrated in FIG. 5 and might be, for example, "L-shaped," oval-shaped, etc.

Figure 6:
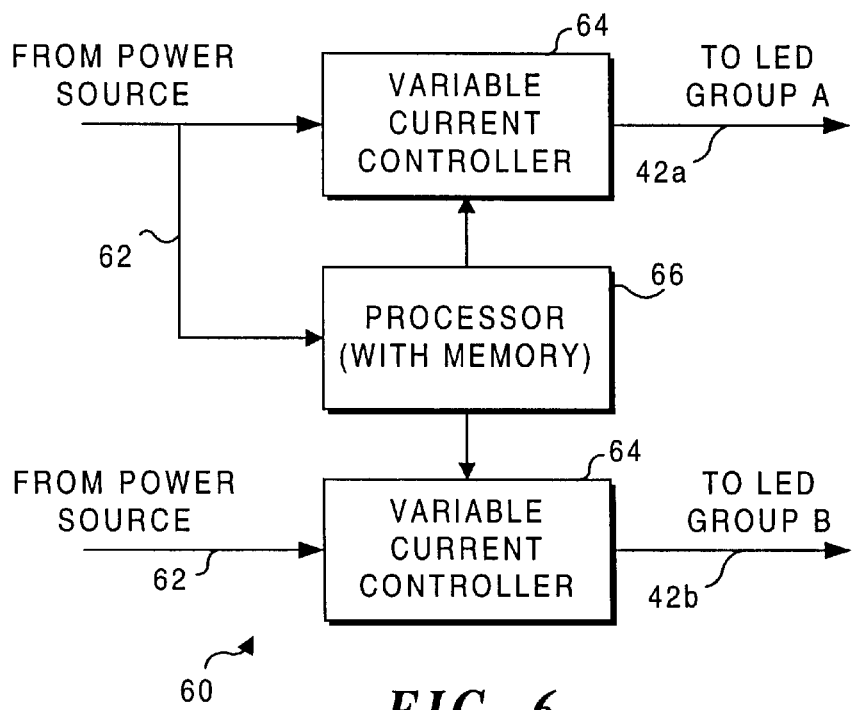
FIG. 6 is a schematic block diagram illustrating the functional components of a microcontroller for the flexible patch.

FIG. 6 illustrates functional components of a microcontroller circuit 60 for use in selectively controlling the electrical currents supplied to each group of LEDs or other light emitting sources. Lines 62 convey the electrical power from the power source to a variable current controller 64 and to a processor 66. Preferably, processor 66 comprises a simple microcontroller that includes both random access memory (RAM) and read only memory (ROM). Stored within the ROM is a simple operating system and a control application program comprising machine instructions that enable basic electrical current control functions to be implemented according to a time schedule and/or determining relative levels of electrical current to be supplied to each of a plurality of different groups of light emitting sources. In the simple case illustrated in FIG. 6, the electrical current supplied to only two different groups of LEDs is controlled. However, it will be apparent that the electrical current supplied to additional groups of LEDs or other light emitting sources can be controlled to provide a desired light intensity and/or to determine a schedule for energizing each group. Variable current controller 64 may comprise voltage controlled variable resistors, or pulse width modulation circuits for use in determining an amplitude or duration of the electrical current supplied to each group in response to a signal supplied by the processor. If pulse width modulation control is employed, the frequency of the pulses or a proportion of their time-on-versus-time-off will determine the light intensity of the light emitting sources. The signal provided by the processor can also determine when and whether each group of light emitting sources is energized. Other control schemes can also be employed for modifying the light output of the light sources in different areas of the undersurface of the flexible patch.

Figure 7A:
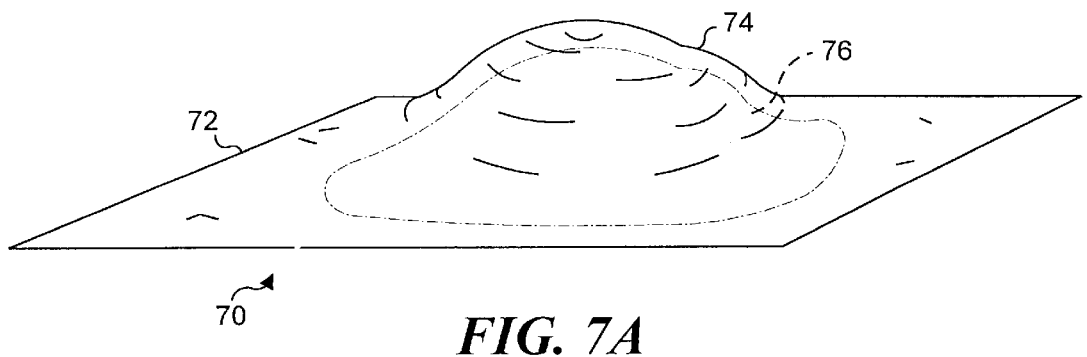
FIG. 7A is a schematic isometric view of a portion of a patient's body at a treatment site where a subdermal tumor is disposed, causing the external surface of the dermal layer overlying the tumor to extend outwardly.
Figure 7B:
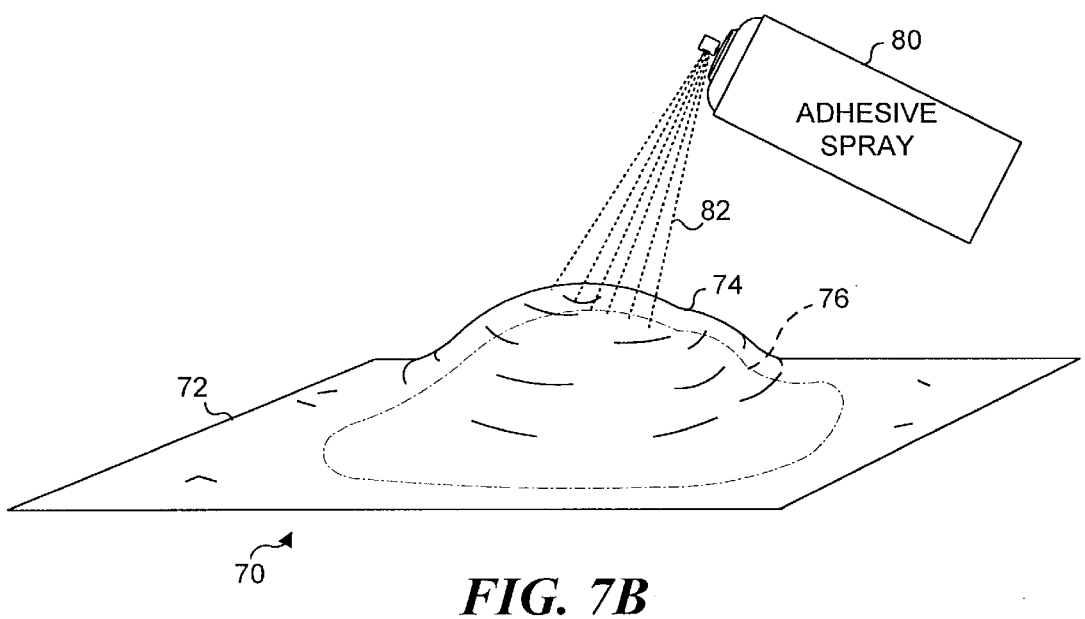
FIG. 7B illustrates the application of an adhesive spray to the treatment site of FIG. 7A for adhering the flexible patch to the treatment site.
Figure 8:
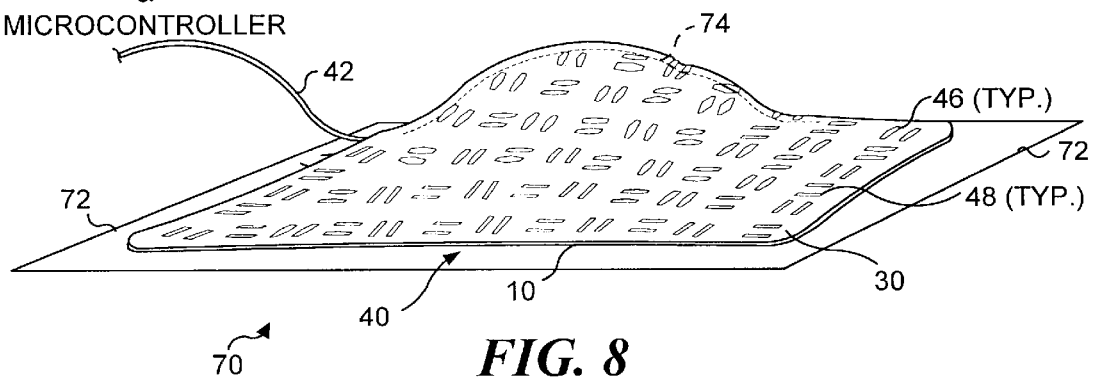
FIG. 8 illustrates the flexible patch conformed and adhered to the non-planar treatment site illustrated in FIGS. 7A and 7B.

FIGS. 7A and 7B illustrate a treatment site 70 in which a subdermal tumor 76 is disposed under the surface of skin 72, forming a convex and generally circular lump 74 that protrudes outwardly. The treatment site at lump 74 is thus clearly non-planar. An adhesive can be applied to the undersurface of flexible patch 40 to secure the flexible patch securely to the treatment site, so that the flexible patch conforms around the lump, as shown in FIG. 8. Alternatively, FIG. 7B illustrates how an adhesive spray can 80 is used to spray an adhesive 82 over the outer surface of the treatment site to adherently attach flexible patch 40 thereto. Provision of the horizontal and vertical slots in flexible patch 40 and its relatively thin cross section enable it to deform and readily conform to the non-planar shape of the treatment site so that the flexible patch molds closely to the underlying surface of skin 72 and molds smoothly over lump 74. Since each of the LEDs are thus disposed immediately adjacent the treatment site, against the surface of the patient's skin, the light emitted thereby is readily able to penetrate through the cutaneous layer and reach subdermal tumor 76 to render PDT (or other light therapy).

Generally, when PDT is being administered to the treatment site, subdermal tumor 76 will have previously been infused with a photoreactive agent that has a characteristic absorption waveband corresponding to that of the light emitted by the plurality of LEDs on the undersurface of flexible patch 40. When activated by that light, the photoreactive agent destroys the abnormal tumor tissue.

In this example, the electrical current supplied to the central group of light sources of the flexible patch that overlie the thickest portion of subdermal tumor 76 should be controlled to provide the maximum intensity and/or duration of light therapy administered thereto. The electrical current supplied to the peripheral group of the light emitting sources can be lower than that supplied to the group of light sources at the center of the flexible patch and/or its duration can be substantially shorter, since the tumor is relatively thinner around the edges. By controlling the light intensity or duration of light therapy applied to the treatment site in this manner, a more effective treatment is achieved and the normal tissue overlying the tumor does not receive an unnecessary exposure to higher intensity light and/or the length of exposure to the light required to treat the central portion of the tumor.

The present invention can also be employed to provide therapy at an internal treatment site within a patient's body. For example, flexible patch 40 can be inserted inside the patient's body through an incised opening and advanced to an internal treatment site, such as the surface of the pancreas, liver, or other organ having a rounded surface. A suitable temporary tissue adhesive such as FOCALSEAL™, or a fibrin glue can be applied to the surface of the organ or to a surface adjacent the internal treatment site within the body to adhesively mount the flexible patch. Alternatively, the tissue adhesive can be applied to the surface of the flexible patch to enable it to adhere to the internal tissue. The openings in the flexible patch again enable it to conform to the rounded non-planar shape of the organ or tissue surface on which it is mounted, greatly facilitating the effective administration of light therapy to the treatment site.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A light therapy patch adapted to conform to a non-planar portion of a patient's body to which a light therapy is to be administered at a treatment site, comprising:
   (a) a flexible substrate formed of a dielectric material, said substrate including a plurality of openings that extend therethrough, said flexible substrate being sufficiently thin and said plurality of openings being sized and configured so as to adapt and enable said flexible substrate to substantially fully conform to a non-planar irregular surface at the treatment site, said plurality of openings further providing ventilation paths for air and moisture to move through the flexible substrate;
   (b) a power source for supplying an electrical current at a desired voltage;
   (c) a plurality of flexible conductive traces applied to at least one surface of the flexible substrate, said flexible conductive traces defining an electrical circuit for conveying an electrical current provided by the power source to defined portions of said at least one surface; and
   (d) a plurality of light emitting sources mounted to the flexible substrate in a spaced apart array and electrically coupled to the conductive traces to receive the electrical current, said electrical current energizing the plurality of light emitting sources so that they emit light to provide the light therapy at the treatment site.

2. The light therapy patch of claim 1, wherein the plurality of conductive traces comprise a conductive fluid applied to said at least one surface of the flexible substrate, said conductive fluid setting to form the conductive traces.

3. The light therapy patch of claim 2, wherein the conductive fluid comprises a conductive ink.

4. The light therapy patch of claim 1, further comprising an adhesive that is adapted to secure the flexible substrate to the non-planar portion of the patient's body, with the flexible substrate conforming thereto.

5. The light therapy patch of claim 4, wherein said flexible substrate is adapted to be adhesively adhered to the non-planar irregular surface at the treatment site with the adhesive, said adhesive being applied to the non-planar irregular surface.

6. The light therapy patch of claim 4, wherein the adhesive is disposed over a surface of the flexible substrate that is adapted to face toward the non-planar portion of the patient's body when the flexible substrate is conformed to said non-planar portion.

7. The light therapy patch of claim 4, wherein the adhesive is adapted to adhere to tissue inside the patient's body, enabling the flexible substrate to be secured to administer the light therapy to an internal treatment site.

8. The light therapy patch of claim 1, further comprising a light reflective layer disposed over a surface of the flexible substrate that faces outwardly when the flexible substrate is conformed to the non-planar portion of the patient's body, said light reflective layer serving to reflect light emitted by the plurality of light sources toward the treatment site.

9. The light therapy patch of claim 1, further comprising an optically transparent coating applied over the plurality of light sources mounted on the flexible substrate to protect the plurality of light sources.

10. The light therapy patch of claim 1, wherein the power source comprises a flexible polymeric battery.

11. The light therapy patch of claim 10, further comprising a lead for connecting the flexible polymeric battery to said plurality of conductive traces, said flexible polymeric battery being carried separate from the flexible substrate by the patient during administration of the light therapy.

12. The light therapy patch of claim 1, wherein the plurality of light emitting sources emit a broad spectrum light.

13. The light therapy patch of claim 1, wherein the plurality of light emitting sources are selected from the group consisting of incandescent lights, halogen lights, fluorescent lights, electroluminescent lights, light emitting diodes, polymeric light emitting diodes, organic light emitting diodes, and metallic light emitting diodes.

14. The light therapy patch of claim 1, wherein the electrical circuit comprises plurality of separate circuits conveying the electrical current to independent groups of the light sources.

15. The light therapy patch of claim 14, further comprising a microcontroller coupled to the electrical circuit for separately controlling the electrical current supplied to each of said independent groups of light sources and thereby controlling the light administered to different regions of the treatment site by the independent groups of light sources.

16. The light therapy patch of claim 1, wherein the flexible substrate has a thickness of approximately 1.0 millimeter or less.

17. A method for administering a light therapy to a treatment site, comprising the steps of:
   (a) providing a vapor permeable patch on which are mounted an array of spaced-apart light sources, said vapor permeable patch comprising a plurality of openings extending therethrough that are sized and configured such that said vapor permeable patch is sufficiently flexible to fully conform to a substantially non-planar portion of a patient's body;
   (b) adhesively attaching and conforming the patch to the patient's body, adjacent to the treatment site; and
   (c) energizing the plurality of light sources to administer the light therapy to the treatment site.

18. The method of claim 17, further comprising the step of providing an ambulatory power source that is coupled to the plurality of light sources on the vapor permeable patch.

19. The method of claim 17, wherein the plurality of light sources are divided into a plurality of separate groups, further comprising the step of selectively controlling an electrical current supplied to each of the separate groups of the light sources to separately control an intensity of light administered to different regions of the treatment site.

20. The method of claim 17, further comprising the step of applying an adhesive to a surface of the treatment site to adhere the vapor permeable patch thereto.

21. The method of claim 17, wherein the plurality of light sources are covered by an optically transparent protective layer on the vapor permeable patch.

22. The method of claim 17, wherein the vapor permeable patch includes an electrical circuit defined by a plurality of conductive traces that are applied to a surface of said patch.

23. The method of claim 22, wherein the plurality of conductive traces are applied to said surface as a fluid.

24. The method of claim 23, wherein the fluid comprises a conductive ink.

25. The method of claim 17, further comprising the step of reflecting light emitted by the plurality of light sources towards the treatment site.

26. The method of claim 17, further comprising the step of administering the light therapy to the treatment site with the vapor permeable patch for an extended period of time, while the patient is ambulatory.

27. The method of claim 17, further comprising the step of providing a coating on the vapor permeable patch having an index of refraction substantially equal to that of skin of the patient.

28. The method of claim 17, further comprising the step of inserting the vapor permeable patch into the patient's body, said step of adhesively attaching and conforming occurring at an internal treatment site within the patient's body.

* * * * *